United States Patent [19]

Junino et al.

[11] Patent Number: 4,863,482
[45] Date of Patent: Sep. 5, 1989

[54] SUBSTITUTED 2-NITRO METAPHENYLENEDIAMINES, A PROCESS FOR THEIR PREPARATION AND THEIR USE IN DYEING KERATINOUS FIBERS, IN PARTICULAR HUMAN HAIR

[75] Inventors: Alex Junino, Livry-Gargan; Nicole Jehanno, Brunoy; Gerard Lang, Saint-Gratien, all of France

[73] Assignee: L'Oreal, Paris, France

[21] Appl. No.: 224,405

[22] Filed: Jul. 26, 1988

[30] Foreign Application Priority Data

Jul. 27, 1987 [LU] Luxembourg .............................. 86951

[51] Int. Cl.$^4$ .......................... A61K 7/13; C07C 149/42
[52] U.S. Cl. .......................................... 8/429; 564/440; 564/441; 8/406; 8/408; 8/415; 8/416; 8/414
[58] Field of Search ..................... 564/440, 441; 8/407, 8/406, 408, 411, 414, 415, 416, 429

[56] References Cited

FOREIGN PATENT DOCUMENTS 0203446 12/1986 European Pat. Off. .
2090853 7/1982 United Kingdom .
2186586 8/1987 United Kingdom .
2186587 8/1987 United Kingdom .

*Primary Examiner*—Paul Lieberman
*Attorney, Agent, or Firm*—Cushman, Darby & Cushman

[57] ABSTRACT

A 2-nitro metaphenylenediamine for use in dyeing keratinous fibers, in particular human hair, has the formula:

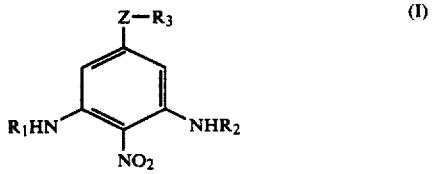

(I)

wherein Z represents a —O—, —S— or —NH— radical. $R_1$, $R_2$ and $R_3$ may be identical or different and represent a hydrogen atom or an alkyl, hydroxyalkyl, polyhydroxyalkyl, alkoxyalkyl or hydroxyalkoxyalkyl radical or an aminoalkyl radical whose amino radical may be mono- or disubstituted by an alkyl or hydroxyalkyl radical. The alkyl and alkoxy radicals contain 1 to 6 carbon atoms. Cosmetically acceptable salts of this compound may also be used.

25 Claims, No Drawings

SUBSTITUTED 2-NITRO METAPHENYLENEDIAMINES, A PROCESS FOR THEIR PREPARATION AND THEIR USE IN DYEING KERATINOUS FIBERS, IN PARTICULAR HUMAN HAIR

BACKGROUND OF THE INVENTION

Field of the Invention

The present invention relates to novel substituted 2-nitro metaphenylenediamines, to a process for their preparation, to dye compositions for keratinous fibers, in particular for human hair containing such fibers, and to a dyeing process using such dye compositions.

Nitrated derivatives of the benzene series are well known in the art for producing in hair a direct dye or complementary highlights in oxidation dyeing.

For direct dyeing, the applicant's French patents FR-1 508 405 and FR-1 584 965 have already advocated the use of 4-nitro metaphenylenediamines substituted in the 6-position, if desired, by lower alkyl or alkoxy radicals or by a halogen atom.

SUMMARY OF THE INVENTION

During research the applicant has discovered that capillary dyes having very good stability towards light, washing and bad weather can be obtained using a particular family of substituted 2-nitro metaphenylenediamines having the formula:

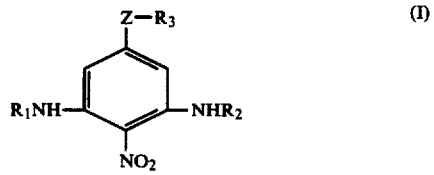

wherein Z represents —O—, —S— or —NH— and $R_1$, $R_2$ and $R_3$ may be identical or different and represent a hydrogen atom or an alkyl, hydroxyalkyl, polyhydroxyalkyl, alkoxyalkyl or aminoalkyl radical where the amino radical may be mono- or disubstituted by an alkyl or hydroxyalkyl radical.

The alkyl and alkoxy radicals mentioned above contain one to six carbon atoms.

Thus the object of the invention is to provide novel compounds of formula (I) as well as their cosmetically acceptable salts.

Particularly preferred $R_1$, $R_2$ and $R_3$ groups include hydrogen and methyl, ethyl, n-propyl, n-butyl, β-hydroxyethyl, β-hydroxypropyl, γ-hydroxypropyl, β,γ-dihydroxypropyl, methoxyethyl, ethoxyethyl, β-hydroxyethoxyethyl, β-aminoethyl, β-hydroxyethylaminoethyl or β-diethylaminoethyl radicals.

Particularly preferred compounds of formula (I) according to the invention include 2,6-diamino-4-methoxynitrobenzene; 2,6-diamino-4-hydroxynitrobenzene; 2-(β-hydroxyethyl)amino-6-(β-hydroxyethyl)amino-4-methoxynitrobenzene; 2-[(3-methylamino-5-methylamino-4-nitro)phenoxylethanol; 3-[(3-methylamino-5-methylamino-4-nitro)phenoxy]propane 1,2-diol; 2-methylamino-6-(β-methoxyethyl)amino-4-methoxynitrobenzene; 2-methylamino-6-methylamino-4-(β-hydroxypropyl)aminonitrobenzene; 2-methylamino-6-methylamino-4-(β,γ-dihydroxypropyl)aminonitrobenzene; 2-methylamino-6-methylamino-4-[(β-hydroxyethoxy)ethylamino]nitrobenzene; 2-(β-hydroxyethyl)amino-6-(β-hydroxyethyl)amino-4-(β-aminoethyl)aminonitrobenzene; 2-(β-hydroxyethyl)amino-4-(β-hydroxyethyl)amino-6-(β-hydroxyethyl)aminonitrobenzene; 4-β-methoxyethoxy-2-(β-methoxyethoxy-2-(β-hydroxyethyl)amino-6-(β-hydroxyethyl)aminonitrobenzene; [3-(β-hydroxyethyl)amino-5-(β-hydroxyethyl)amino-4-nitrophenyl]β-hydroxy ethylthioether; 2-(β,γ-dihydroxypropyl)amino-6-(β,γ-dihydroxypropyl)amino-4-methoxynitrobenzene; 2-(γ-hydroxypropyl)amino-4-(γ-hydroxypropyl)amino-6-(γ-hydroxypropyl)aminonitrobenzene; 2-amino-6-(β-hydroxyethyl)amino-4-methoxynitrobenzene and cosmetically acceptable salts of these compounds.

A further object of the invention is a process for the preparation of compounds of formula (I) consisting in disubstituting a 2,4,6-trihalonitrobenzene to obtain a 2,6-diamino-4-halonitrobenzene which is subsequently reacted with $HZR_3$ to obtain the compound of formula (I).

This process may be schematically represented as follows:

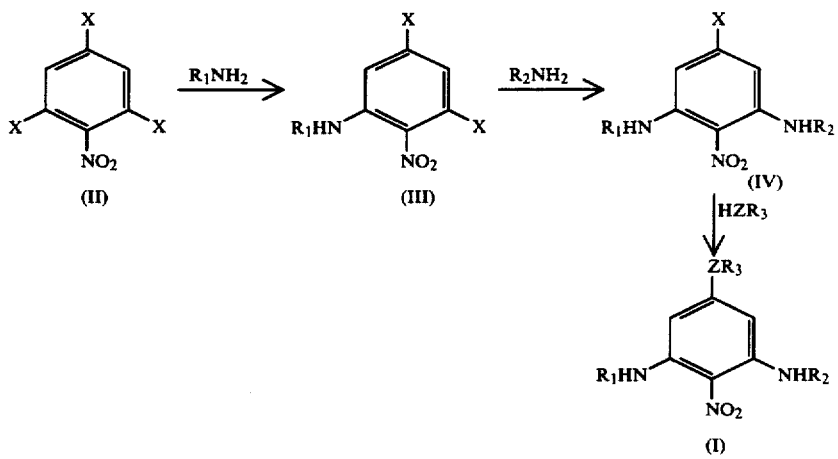

where X represents a halogen atom, particularly chlorine or fluorine, and $R_1$, $R_2$, $R_3$ and Z have the meanings given above.

Compounds of formula (IV) may be prepared by reacting ammonia or an amine of formula $NH_2R_1$, $R_1$ having the meaning given above, with the 2,4,6-trihalonitrobenzene of formula (II) in a first step to obtain compound (III) which is then reacted with an amine $NH_2R_2$ or ammonia in a second step to give compound (IV).

When group $R_2$ is identical to group $R_1$ in compound (IV), the latter can be prepared in a single stage starting from compound (II). Synthesis of 2,6-diamino-4-chloronitrobenzene by the action of ammonia on 2,4,6-trichloronitrobenzene is known (Beil, Vol. 13, p. 58).

Substitution of the halo groups by $NHR_1$ and $NHR_2$ amino groups is effected either in the presence or in the absence of solvents. Solvents in routine use are lower alcohols or solvents such as dimethylformamide, dimethylsulfoxide, N-methylpyrrolidone or N,N'-dimethylpropylene urea. When ammonia or amines $NH_2R_1$ or $NH_2R_2$ are used in aqueous solution, for reasons of solubility it is preferable to add a solvent selected from those cited above.

The reaction temperatures for the substitution of halo groups by $NHR_1$ and/or $NHR_2$ amino groups may vary between $-10°$ C. and the reflux temperature of the $NH_2R_1$ and/or $NH_2R_2$ amine, or that of the solvent. Generally, the temperature is between 20° C. and 170° C.

When gaseous ammonia or $NH_2R_1$, and/or $NH_2R_2$ amines with a low boiling point are used, the substitution may be carried out using an autoclave, a pressure of up to 25 kg/cm² being generally sufficient. Substitution of the halogen atom in the 4 position by the $-ZR_3$ substituent may be conducted in the presence or absence of solvents. Where Z represents $-NH-$, an excess of the amine $H_2NR_3$ is generally used which acts as reactant and solvent.

Where Z represents an oxygen or sulfur atom, the substitution may be carried out in the presence of an alkaline hydroxide or alcoholate, either in the presence of a solvent such as dioxane, N-methylpyrrolidone, and lower alcohols ($C_1$ to $C_4$), or in the absence of solvent using the $HZR_3$ reactant in excess as the solvent.

The reaction temperature lies between 30° and 150° C.

When $-ZR_3$ represents the $-OH-$ radical, compounds of formula

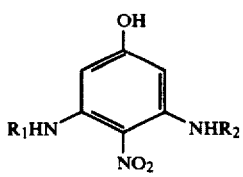

(Ia)

where $R_1$ and $R_2$ represent H or alkyl, are obtained from compounds of formula (I) (where Z is an oxygen atom and $R_3$ represents a methyl radical) by dealkylation with hydrobromic acid at a temperature between 50° and 100° C.

A still further object of the invention is to provide a dye composition for keratinous fibers, in particular human hair, comprising, in a solvent appropriate to dyeing keratinous fibers, at least one direct dye having formula (I), these dye compositions operating in a direct dyeing process or oxidation dyeing process.

A further object of the invention is thus constituted by a process for dyeing keratinous fibers, particularly human hair, using a dye composition containing the dye of formula (I).

Dye compositions in accordance with the invention contain, in a solvent medium, at least one compound corresponding to formula (I) or one of its cosmetically acceptable salts, and may be used for direct dyeing of keratinous fibers or for oxidation dyeing of these fibers, in which case the compounds having formula (I) produce highlights which complement the base dye obtained by oxidizing development of precursors of oxidation dyes.

Dye compositions according to the invention contain compounds of formula (I) in proportions of between 0.001 and 5% by weight and preferably 0.05 and 2% by weight with respect to the total composition weight.

The solvent medium is preferably a cosmetic vehicle generally constituted by water, however organic solvents may also be added to the compositions in order to solubilize compounds which would not be sufficiently soluble in water. Among these solvents, lower alcohols may be cited, eg. ethanol, isopropanol, aromatic alcohols such as benzyl alcohol and phenoxyethanol, polyols such as glycerol, glycols and their ethers such as 2-butoxyethanol or 2-ethoxyethanol, ethyleneglycol, propyleneglycol, the monomethyl and monoethyl ethers of diethyleneglycol, also their analogs amd mixtures. Preferably, these solvents are present in proportions of from 1 to 75% by weight and particularly from 5 to 50% by weight with respect to the total composition weight.

These compositions may contain surface-active agents which may be anionic, cationic, non-ionic or amphoteric in nature and may be mixed. These surface-active agents are present in the inventive compositions in proportions of between 0.5 and 55% by weight and preferably of 4 and 40% by weight with respect to the total composition weight.

The compositions can be thickened, preferably using compounds selected from sodium alginate, gum arabic, xanthane gum, cellulose derivatives such as methylcellulose, hydroxyethylcellulose, hydroxypropyl methylcellulose and carboxymethylcellulose, and various polymers having thickening properties such as, most particularly, acrylic acid derivatives. Mineral thickening agents such as bentonite can also be used. These thickening agents are preferably present in proportions of between 0.1 and 10% by weight and particularly between 0.5 and 2% by weight with respect to the total composition weight.

Compositions according to the invention may also contain various other additives normally in use in hair dye compositions, particularly penetrating agents, dispersing agents, sequestrating agents, film formers, buffers and fragrances.

The compositions may be in various forms, for example liquids, creams, gels or any other appropriate form for dyeing hair. In addition they may be packaged in aerosol cans with a propellant.

The dye compositions may have a pH of between 3 and 11.5, preferably between 5 and 11.5. It is adjusted to the desired value using an alkalizing agent such as ammonia, sodium, potassium or ammonium carbonate, sodium or potassium hydroxide, alkanolamines such as mono-, di- or triethanolamine, 2-amino-2-methylpropan-1-ol, 2-amino-2-methylpropane-1,3-diol or alkylamines such as ethylamine or triethylamine. Acidification agents such as phosphoric, hydrochloric, tartaric, acetic, lactic or citric acids may also be used.

When these compositions are intended to be used in a direct hair dyeing process, as well as compounds according to the invention, they may contain other direct dyes such as azo dyes or anthraquinone dyes, for example 1,4,5,8-tetraaminoanthraquinone, indophenols, indoanilines and nitro dyes of the benzene series other than compounds of formula (I).

The concentrations of these other direct dyes may be between 0.001 and 5% by weight with respect to the total composition weight.

These compositions, used in a direct dyeing process, are applied to the keratinous fibers for an application period of 5 to 50 minutes, the fibers are rinsed then washed by shampooing if desired, rinsed again and dried.

Compositions according to the invention may also be used in the form of capillary setting lotions intended simultaneously to improve the setting lotion hold and to lightly color or highlight the hair. In this case they may be in the form of aqueous, alcoholic or hydroalcoholic solutions containing at least one cosmetic resin.

They are applied to washed and rinsed, wet hair, set if desired then dried.

The following cosmetic resins may in particular be used in setting lotions: polyvinylpyrrolidone; crotonic acid-vinyl acetate copolymer; vinylpyrrolidone-vinyl acetate copolymer; the semi-esters of maleic anhydride-butylvinyl ether or maleic anhydride-methylvinyl ether or copolymers of maleic acid and methylvinylether or butylvinylether. Any other cationic, anionic, non-ionic or amphoteric polymer normally used in this type of composition may also be used. These cosmetic resins may be present in the inventive compositions at concentrations of 0.1 to 4% by weight, preferably 1 to 3% by weight with respect to total composition weight.

When compositions according to the invention constitute oxidation dyes involving color revelation by an oxidant, compounds of formula (I) are primarily used to endow the final color with highlights.

In association with at least one nitro dye of formula (I) and, if desired, other direct dyes, these compositions thus contain oxidation dye precursors.

They may contain, for example, paraphenylenediamines such as: paraphenylenediamine; paratoluylenediamine; 2-chloroparaphenylenediamine; 2,6-dimethylparaphenylenediamine; 2,6-dimethyl-3-methoxyparaphenylenediamine; N-(β-methoxyethyl)paraphenylenediamine; N,N-(β-hydroxyethyl)paraphenylenediamine; or N,N-(ethyl,carbamylmethyl)-4-amino aniline and their salts.

They may also contain paraaminophenols, for example: paraaminophenol; N-methylparaaminophenol; 2-chloro-4-aminophenol; 3-chloro-4-aminophenol; or 2-methyl-4-aminophenol and their salts.

They may also contain orthoaminophenol.

They may also contain heterocyclic derivatives, for example 2,5-diaminopyridine or 7-aminobenzomorpholine.

In association with oxidation dye precursors, compositons according to the invention may contain couplers which are well known in the art.

The following couplers in particular may be mentioned: metadiphenols; metaaminophenols and their salts; metaphenylenediamines and their salts; metacyclaminophenols; metaureidophenols and metacarbalkoxyaminophenols.

Finally, further couplers which may be used in the inventive compositions are: α-naphthol; couplers having an active methylene group such as diketonic compounds and pyrazolones and heterocyclic couplers such as pyridine and benzomorpholine derivatives.

As well as oxidation dye precursors, these compositions contain reducing agents in proportions of between 0.05 and 3% by weight with respect to total composition weight.

Oxidation dye precursors in the inventive compositions may be used at concentrations of between 0.001 and 5% by weight and preferably between 0.03 and 2% by weight with respect to total composition weight.

The couplers may also be present in proportions of between 0.001 and 5% by weight, preferably between 0.015 and 2% by weight. The pH of these oxidation dye compositions is preferably between 7 and 11.5 and is adjusted using the alkalizing agents defined above.

A process for dyeing keratinous fibers, particularly human hair, involving color revelation by an oxidant, consists in applying to the fibers the dye composition comprising both a dye according to the invention and dye precursors. Color development may occur slowly in the presence of atmospheric oxygen, but preferably a chemical color revealing system is used, most frequently selected from hydrogen peroxide, urea peroxide and peroxy salts. In particular, a solution of 20 vol hydrogen peroxide is used.

Once the composition and oxidizing agent has been applied to the keratinous fibers, it is left to take for 10 to 50 minutes, preferably 15 to 30 minutes, after which the keratinous fibers are rinsed, washed by shampooing if required, rinsed again then dried.

The following examples are intended to illustrate the invention without being in any way limiting.

PREPARATION EXAMPLE 1

Preparation of 2,6-diamino-4-methoxynitrobenzene

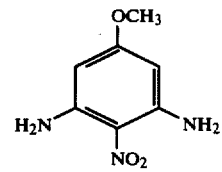

Stage 1

Preparation of 2,6-diamino-4-chloronitrobenzene 0.34 mole (76 g) of 2,4,6-trichloronitrobenzene was added to 400 ml of 28% ammonia in water and 100 ml of ethanol in an autoclave. The reaction medium was heated for 16 hours at 155° C.–160° C. at a pressure of 20 kg/cm². After cooling, the desired product precipitated out. After filtering and remixing with water until the washings were neutral, it was dried under vacuum in the presence of phosphorus pentoxide. After recrystallization from isopropanol to remove any resin, it melted at 202° C. (literature 192° C.–194° C.).

Analysis of the product obtained yielded the following results:

| Analysis | Calculated for $C_6H_6ClN_3O_2$ | Found |
|---|---|---|
| C % | 38.40 | 38.55 |
| H % | 3.20 | 3.26 |
| N % | 22.40 | 22.43 |
| O % | 17.06 | 16.88 |
| Cl % | 18.93 | 18.74 |

Stage 2

Preparation of 2,6-diamino-4-methoxynitrobenzene 0.024 mole (4.5 g) of 2,6-diamino-4-chloronitrobenzene in 9 ml of N-methylpyrrolidone and 22.5 ml of 30% sodium methylate in methanol were refluxed for 4 hours 30 minutes. Upon dilution of the reaction medium with water, the desired product precipitated out. After filtering, water washing and vacuum drying in the presence of $P_2O_5$, the product obtained was recrystallized from toluene; a black insoluble product was eliminated by hot filtration. The desired product melted at 140° C.

Analysis of the product obtained yielded the following results:

| Analysis | Calculated for $C_7H_9N_3O_3$ | Found |
|---|---|---|
| C % | 45.90 | 45.86 |
| H % | 4.96 | 4.91 |
| N % | 22.95 | 22.87 |
| O % | 26.23 | 26.52 |

PREPARATION EXAMPLE 2

Preparation of 2-(β-hydroxyethyl)amino-6-(β-hydroxyethyl)amino-4-methoxynitrobenzene

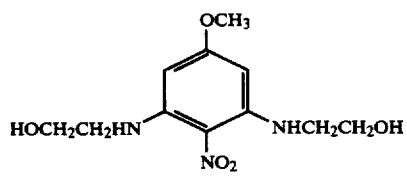

Stage 1

Preparation of 2-(β-hydroxyethyl)amino-6-(β-hydroxyethyl)amino-4-chloronitrobenzene 0.132 mole (30 g) of 2,4,6-trichloronitrobenzene were heated at 95° C. in 120 ml of ethanolamine. After 30 minutes the reaction medium was poured over 240 g of an ice-water mixture. The desired product precipitated out and was filtered, washed with water and then dried under vacuum in the presence of phosphorus pentoxide. After recrystallization from absolute ethanol, it melted at 154° C.

Analysis of the product obtained yielded the following results:

| Analysis | Calculated for $C_{10}H_{14}ClN_3O_4$ | Found |
|---|---|---|
| C % | 43.56 | 43.37 |
| H % | 5.08 | 5.11 |
| N % | 15.24 | 15.25 |
| O % | 23.23 | 23.45 |
| Cl % | 12.88 | 13.01 |

Stage 2

Preparation of 2-(βhydroxyethyl)amino-6-(β-hydroxyethyl)amino-4-methoxynitrobenzene 0.09 mole (25 g) of 2-(β-hydroxyethyl)amino-6-(β-hydroxyethyl)amino-4-chloronitrobenzene in 100 ml of a 25% sodium methylate solution in methanol was heated over a boiling water bath. After heating for 1 hour 30 minutes the desired product was precipitated out of the reaction medium by adding 250 g of ice water. After filtering and hot drying under vacuum in the presence of $P_2O_5$, the desired product was recrystallized from 96° ethanol. It melted at 150° C.

Analysis of the product obtained yielded the following results:

| Analysis | Calculated for $C_{11}H_{17}N_3O_5$ | Found |
|---|---|---|
| C % | 48.70 | 48.91 |
| H % | 6.32 | 6.41 |
| N % | 15.49 | 15.61 |
| O % | 29.49 | 29.30 |

PREPARATION EXAMPLE 3

Preparation of 2-[(3-methylamino-5-methylamino-4-nitro)phenoxy]ethanol

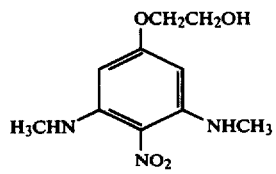

Stage 1

Preparation of 4-chloro-2-methylamino-6-methylaminonitrobenzene 0.150 mole (34 g) of 2,4,6-trichloronitrobenzene was added, portionwise and at room temperature, to 300 ml of a solution of 30% methylamine in absolute ethanol. After 23 hours agitation at room temperature the precipitate, consisting primarily of 4-chloro-2-methylamino-6-methylaminonitrobenzene, was filtered. It was chromatographically pure and melted at 193° C.

Stage 2

Preparation of 2-[(3-methylamino-5-methylamino-4-nitro)phenoxy]ethanol 0.031 mole (28.3 g) of 4-chloro-2-methylamino-6-methylaminonitrobenzene was added portionwise to a solution of 17.2 g of pelletized potash in 66 ml of ethyleneglycol and 100 ml of N-methylpyrrolidone at 50° C. This was heated for 3 hours over a boiling water bath. The desired product was precipitated out on addition of 300 g of ice water. After filtering and drying under vacuum in the presence of $P_2O_5$, it was recrystallized from 96° ethanol. It melted at 142° C.

Analysis of the product obtained yielded the following results:

| Analysis | Calculated for $C_{10}H_{15}N_3O_4$ | Found |
|---|---|---|
| C % | 49.78 | 49.73 |
| H % | 6.27 | 6.28 |
| N % | 17.42 | 17.38 |
| O % | 26.53 | 26.64 |

PREPARATION EXAMPLE 4

Preparation of
3-[(3-methylamino-5-methylamino-4-nitro)
phenoxy]-propane 1,2-diol

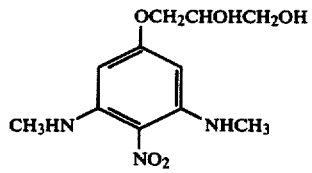

Stage 1

Preparation of
2-methylamino-6-methylamino-4-fluoronitro benzene 11 ml of 2,4,6-trifluoronitrobenzene was added dropwise to 65 ml of a solution of 25% methylamine in absolute ethanol, maintaining the temperature between −10° C. and 0° C. by cooling. Once the addition was complete, the reaction medium was left for 1 hour at room temperature. The desired product which had crystallized out of the reaction medium was filtered, washed and then heat dried under vacuum in the presence of $P_2O_5$. It melted at 198° C.

Analysis of the product obtained yielded the following results:

| Analysis | Calculated for $C_8H_{10}N_3O_2F$ | Found |
|---|---|---|
| C % | 48.24 | 48.13 |
| H % | 5.02 | 5.03 |
| N % | 21.10 | 21.02 |
| O % | 9.55 | 9.62 |

Stage 2

Preparation of
3-[(3-methylamino-5-methylamino-4-nitro)phenoxy]-propane 1,2 diol A solution of 880 mg of pelletized soda in 8 g of glycerol diluted with 0.3 ml of water at 90° C. was added to a solution of 0.01 mole 2-methylamino-6-methyl amino-4-fluoronitrobenzene in 8 g of glycerol preheated to 90° C. After 2 hours' heating over a boiling water bath the reaction mixture was heated for 20 minutes at 130° C. The desired product precipitated out of the reaction medium after dilution with 20 ml of ice water. After vacuum drying it was recrystallized from isopropanol, then washed with refluxing ethyl acetate. It melted at 155° C.

Analysis of the product obtained yielded the following results:

| Analysis | Calculated for $C_{11}H_{17}N_3O_5$ | Found |
|---|---|---|
| C % | 48.71 | 48.84 |
| H % | 6.27 | 6.39 |
| N % | 15.50 | 15.40 |
| O % | 29.52 | 29.39 |

PREPARATION EXAMPLE 5

Preparation of 2,6-diamino-4-hydroxynitrobenzene

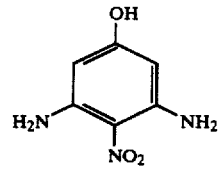

1 g of 2,6-diamino-4-methoxynitrobenzene prepared as in example 1 was heated in 3 ml of 66% hydrobromic acid for 15 minutes over a boiling water bath. Upon addition of water the desired product precipitated as the hydrobromate. This was taken up into suspension in water then dissolved by addition of concentrated soda in order to enable elimination of an insoluble impurity by filtration in the presence of animal charcoal. The desired product precipitated from the filtrate on addition of concentrated hydrochloric acid. After filtration and vacuum drying in the presence of $P_2O_5$, the product decomposed at 264° C.

Analysis of the desired product yielded the following results:

| Analysis | Calculated for $C_6H_7N_3O_3$ | Found |
|---|---|---|
| C % | 42.60 | 42.51 |
| H % | 4.17 | 4.22 |
| N % | 24.85 | 24.73 |
| O % | 28.38 | 28.28 |

PREPARATION EXAMPLE 6

Preparation of
2-methylamino-6-methylamino-4-(β-hydroxypropyl)-aminonitrobenzene

0.01 mole (2 g) of 2-methylamino-6-methylamino-4-fluoronitrobenzene in 8 ml of 1-amino-2-propanol was brought to 100° C. under agitation. After 15 minutes' heating, the reaction medium was diluted with 10 ml of water and neutralized by addition of hydrochloric acid. The precipitated desired product was filtered. After drying, it was recrystallized from 96° ethanol. It melted at 231° C.

Analysis of the desired product yielded the following results:

| Analysis | Calculated for $C_{11}H_{18}N_4O_3$ | Found |
|---|---|---|
| C % | 51.97 | 52.02 |
| H % | 7.09 | 7.16 |
| N % | 22.05 | 21.92 |
| O % | 18.90 | 19.07 |

Preparation Example 7

Preparation of 2-methylamino-6-methylamino-4-(β,γ-dihydroxypropyl)-aminonitrobenzene

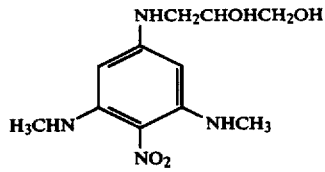

A mixture of 0.01 mole (2 g) of 2-methylamino-6-methylamino-4-fluoronitrobenzene and 38 g of 3-amino propane 1,2-diol in 7 ml of dioxan diluted with 1 ml of N-methylpyrrolidone was refluxed for 15 hours.

The reaction medium was diluted with 20 ml of ice water. The desired product precipitated out. After washing and vacuum drying in the presence of $P_2O_5$ it was recrystallized from 96° ethanol. The product melted at 210° C.

Analysis of the product obtained yielded the following results:

| Analysis | Calculated for $C_{11}H_{18}N_4O_4$ | Found |
|---|---|---|
| C % | 48.89 | 48.94 |
| H % | 6.67 | 6.59 |
| N % | 20.74 | 20.67 |
| O % | 23.70 | 23.53 |

PREPARATION EXAMPLE 8

Preparation of 2-methylamino-6-methylamino-4-[(β-hydroxy ethoxy)ethyl]aminonitrobenzene

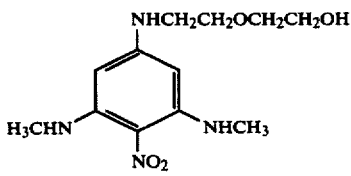

0.01 mole (2 g) of 2-methylamino-6-methylamino-4-fluoronitrobenzene in 8 ml of 2-(2-aminoethoxy)ethanol was heated to 100° C. After 30 minutes the reaction medium was diluted with 20 ml of ice water and the desired product precipitated out. After filtering and vacuum drying in the presence of $P_2O_5$, it was recrystallized from isopropanol and then from ethyl acetate. The product melted at 132° C.

Analysis of the product obtained yielded the following results:

| Analysis | Calculated for $C_{12}H_{20}N_4O_4$ | Found |
|---|---|---|
| C % | 50.69 | 50.65 |
| H % | 7.09 | 7.08 |
| N % | 19.71 | 19.65 |
| O % | 22.51 | 22.81 |

PREPARATION EXAMPLE 9

Preparation of 2-methylamino-6-(β-methoxyethyl)amino-4-methoxynitrobenzene

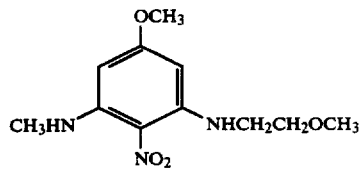

Stage 1

Preparation of 2-methylamino-4,6-dichloronitrobenzene

The same method as that in stage 1 of example 3 was used.

After filtering the precipitate constituted by 4-chloro-2-methylamino-6-methylaminonitrobenzene, the filtrate was recovered and evaporated to dryness under reduced pressure. 800 ml of concentrated hydrochloric acid was added to the dry extract thus obtained and the insoluble fraction eliminated by filtration. Following dilution of the filtrate in 650 ml of water the desired product precipitated out. This was diluted with water then vacuum dried in the presence of $P_2O_5$. After recrystallization from isopropanol then absolute ethanol, the product had a melting point of 120° C.

Analysis of the product obtained yielded the following results:

| Analysis | Calculated for $C_7H_6Cl_2N_2O_2$ | Found |
|---|---|---|
| C % | 38.01 | 38.02 |
| H % | 2.71 | 2.72 |
| N % | 12.67 | 12.77 |
| O % | 14.48 | 14.40 |
| Cl % | 32.13 | 32.01 |

Stage 2

Preparation of 2-methylamino-6-(β-methoxyethyl)amino-4-chloronitrobenzene 0.09 mole (20 g of 2-methylamino-4,6-dichloro nitrobenzene was added portionwise to 80 ml of 2-methoxyethyl amine preheated to 80° C. After 2 hours' heating, the reaction medium was diluted with 100 ml of ice water and the desired product precipitated out. After filtering, water washing then vacuum drying in the presence of $P_2O_5$, it was recrystallized from 96° ethanol. It melted at 93° C.

Analysis of the product obtained yielded the following results:

| Analysis | Calculated for $C_{10}H_{14}ClN_3O_3$ | Found |
|---|---|---|
| C % | 46.24 | 46.25 |
| H % | 5.40 | 5.35 |
| N % | 16.18 | 16.24 |
| O % | 18.50 | 18.61 |
| Cl % | 13.68 | 13.52 |

Stage 3

Preparation of 2-methylamino-6-(β-methoxyethyl)amino-4-methoxynitrobenzene 0.019 mole (5 g) of 2-methylamino-6-(β-methoxyethyl)amino-4-chloronitrobenzene was refluxed with 35 ml of 26% sodium methylate in methanol for 45 minutes then diluted with 100 ml of ice water to precipitate the desired product. Following filtering, water washing and drying under vacuum in the presence of $P_2O_5$, the product obtained was recrystallized from isopropanol. It melted at 84° C.

Analysis of the product obtained yielded the following results:

| Analysis | Calculated for $C_{11}H_{17}N_3O_4$ | Found |
|---|---|---|
| C % | 51.76 | 51.75 |
| H % | 6.67 | 6.71 |
| N % | 16.47 | 16.46 |
| O % | 25.10 | 24.99 |

PREPARATION EXAMPLE 10

Preparation of 2-(β-hydroxyethyl)amino-6-(β-hydroxyethyl)amino-4-(β-aminoethyl)aminonitrobenzene

0.13 mole (36.5 g) of 2-(β-hydroxyethyl)amino-6-(β-hydroxyethyl)amino-4-chloronitrobenzene, whose synthesis was described in stage 1 of example 2, was heated for 2 hours at 130° C. in 150 ml of ethylenediamine, then the reaction medium diluted with 450 ml of ice water to precipitate out the desired product. After filtering and water washing to neutrality, the product obtained was dried under vacuum in the presence of $P_2O_5$. It was recrystallized from 96° ethanol and melted at 220° C.

Analysis of the product obtained yielded the following results:

| Analysis | Calculated for $C_{12}H_{21}N_5O_4$ | Found |
|---|---|---|
| C % | 48.16 | 48.14 |
| H % | 7.02 | 7.07 |
| N % | 23.41 | 23.26 |
| O % | 21.40 | 21.62 |

PREPARATION EXAMPLE 11

Preparation of 2-(β-hydroxyethyl)amino-4-(β-hydroxyethyl)amino-6-(β-hydroxyethyl)aminonitrobenzene

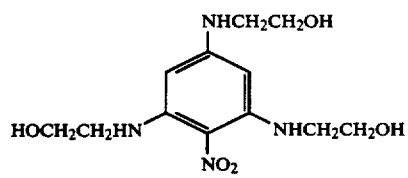

0.0072 mole (2 g) of 2-(β-hydroxyethyl)amino-6-(β-hydroxyethyl)amino-4-chloronitrobenzene, synthesized in stage 1 of example 2, was heated at 100°-110° C. with 6 ml of ethanolamine for 6 hours. The reaction medium was diluted with ice water then brought to neutrallity by addition of concentrated hydrochloric acid to precipitate out the desired product. After filtering and hot drying under vacuum in the presence of $P_2O_5$, it was recrystallized from 96° ethanol. It melted at 200° C.

Analysis of the product obtained yielded the following results:

| Analysis | Calculated for $C_{12}H_{20}N_4O_5$ | Found |
|---|---|---|
| C % | 48.00 | 47.95 |
| H % | 6.67 | 6.50 |
| N % | 18.67 | 18.64 |
| O % | 26.66 | 26.78 |

PREPARATION EXAMPLE 12

Preparation of [3-(β-hydroxyethyl)amino-5-(β-hydroxyethyl)amino-4-nitrophenyl]-β-hydroxyethylthioether

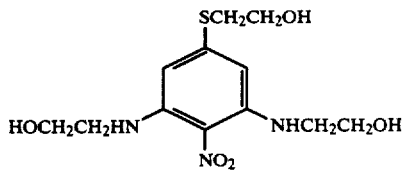

A solution of 7.5 g of pelletized potash dissolved in 9.5 ml of thioethanol was added dropwise to 0.08 mole (22 g) of 2-(β-hydroxyethyl)amino-6-(β-hydroxyethyl)amino-4-chloronitrobenzene (whose synthesis was described in stage 1 of example 2) in 44 ml of absolute ethanol. The reaction medium was refluxed for 2 hours 30 minutes. The desired product precipitated out on cooling. It was filtered then redisposed in water. After drying, it was recrystallized from ethanol. It melted at 157° C.

Analysis of the product obtained yielded the following results:

| Analysis | Calculated for $C_{12}H_{19}N_3SO_5$ | Found |
|---|---|---|
| C % | 45.42 | 45.21 |
| H % | 5.99 | 5.99 |
| N % | 13.25 | 13.18 |
| O % | 25.24 | 25.29 |
| S % | 10.10 | 9.99 |

PREPARATION EXAMPLE 13

Preparation of 2-(γ-hydroxypropyl)amino-4-(γ-hydroxypropyl)amino-6-(γ-hydroxypropyl)aminonitrobenzene

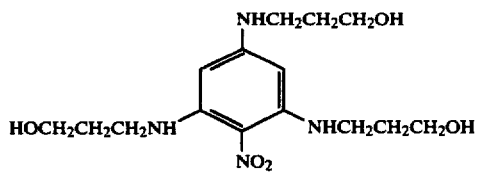

Using the same method as for example 11 replacing ethanolamine by propanolamine, the desired product was crystallized from ethanol and melted at 150° C.

Analysis of the product obtained yielded the following results:

| Analysis | Calculated for $C_{15}H_{26}N_4O_5$ | Found |
|---|---|---|
| C % | 52.62 | 52.68 |
| H % | 7.65 | 7.66 |
| N % | 16.36 | 16.22 |
| O % | 23.37 | 23.37 |

PREPARATION EXAMPLE 14

Preparation of 4-(β-methoxyethoxy)-2-(β-hydroxyethyl)amino-6-(β-hydroxyethyl)aminonitrobenzene

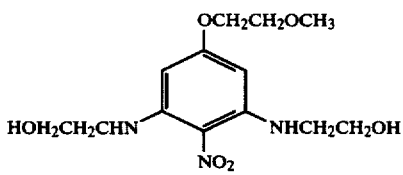

0.09 mole (25 g) of 4-chloro-2-(β-hydroxyethyl)amino-6-(β-hydroxyethyl)aminonitrobenzene, synthesized in stage 1 of example 2, was added to a solution of 11.9 g of pelletized potash in 60 ml of 2-methoxyethanol and 25 ml of N-methylpyrrolidone and heated for 4 hours over a boiling water bath. The reaction medium was diluted with 350 ml of ice water and the desired product obtained by high pressure liquid chromatography (HPLC). About 150 ml of the aqueous solution obtained by dilution of the reaction medium were injected onto a $C_{18}RD$ chromatographic column (Instrument: Waters Prep 500). The desired product was eluted by a 40% methanol—60% water solution. After evaporation of the fractions containing the desired product, a dry extract was obtained which was recrystallized from isopropanol. After recrystallization, it melted at 116° C.

PREPARATION EXAMPLE 15

Preparation of 2-(β,γ-dihydroxypropyl)amino-6-(β,γ-dihydroxypropyl)amino-4-methoxynitrobenzene

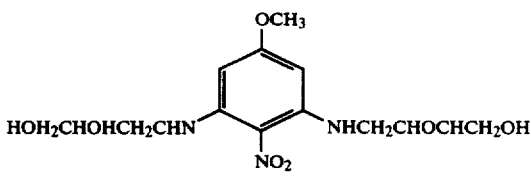

Stage 1

Preparation of 4-chloro-2-(β,γ-dihydroxypropyl)amino-6-(β,γ-dihydroxypropyl)aminonitrobenzene A mixture of 0.1 mole (22.6 g) of 2,4,6-trichloro nitrobenzene and 54.7 g of 3-amino-1,2-propanediol in 20 ml of dioxan was refluxed for 4 hours followed by evaporation of the dioxan under reduced pressure. The oil obtained was diluted in about 300 ml of water. The desired product was obtained using HPLC in two stages. About 200 ml of the aqueous solution of the product containing 3-amino-1,2-propanediol were injected onto a $C_{18}RD$ chromatographic column (Instrument: Waters Prep 500). The desired product was eluted using 35% methanol-65% water solution. After evaporation of the fractions containing the desired product, a dry extract was obtained which was recrystallized from 96° alcohol. The product melted at 146° C.

Analysis of the product obtained yielded the following results:

| Analysis | Calculated for $C_{12}H_{18}N_3O_6Cl$ | Found |
|---|---|---|
| C % | 42.92 | 42.87 |
| H % | 5.36 | 5.37 |
| N % | 12.52 | 12.39 |
| O % | 28.61 | 28.69 |
| Cl % | 10.58 | 10.47 |

Stage 2

Preparation of 2-(β,γ-dihydroxypropyl)amino-6-(β,γ-dihydroxypropyl)amino-4-methoxynitrobenzene 4.56 g of the compound prepared in stage 1 was reflxed for 7 hours with 30 ml of 20% sodium methylate in methanol. After dilution with water and acidification, the methanol was eliminated by evaporation under reduced pressure. After extraction of the evaporation residue with ethyl acetate, a dry extract was obtained which was purified using HPLC (Instrument: Waters Prep 500; $C_{18}RD$ Column;30% methanol-70% water eluant). The desired product melted at 130° C.

PREPARATION EXAMPLE 16

Preparation of 2-amino-6-(β-hydroxyethyl)amino-4-methoxynitrobenzene

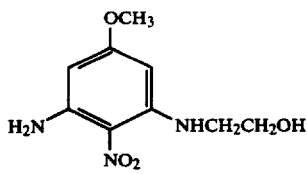

Stage 1

Preparation of 2-amino-6-(β-hydroxyethyl)amino-4-chloronitrobenzene 0.05 mole (11.2 g) of 2-amino-4,6-dichloronitrobenzene (Recueil. Trav. Chim. 68, p. 88 [1949]) in 45 ml of ethanolamine was heated for 2 hours over a boiling water bath. The reaction medium was diluted with 150 ml of ice water. After acidification with 80 ml of hydrochloric acid, the desired product precipitated out. It melted at 183° C. after recrystallization from 400 ml isopropanol.

Analysis of the product obtained yielded the following results:

| Analysis | Calculated for $C_8H_{10}N_3O_3Cl$ | Found |
|---|---|---|
| C % | 41.47 | 41.42 |
| H % | 4.32 | 4.10 |
| N % | 18.14 | 17.98 |
| O % | 20.73 | 20.53 |
| Cl % | 15.33 | 15.18 |

Stage 2

Preparation of 2-amino-6-(β-hydroxyethyl)amino-4-methoxynitrobenzene 0.172 mole (40 g) of 2-amino-6-(β-hydroxyethyl)amino-4-chloronitrobenzene in 160 ml of a 30% solution of sodium methylate in methanol was heated for 2½ hours over a boiling water bath. The desired product precipitated out after dilution with 350 ml of ice water. After recrystallizing from boiling isopropanol to eliminate an insoluble impurity, the desired product melted at 148° C.

Analysis of the product obtained yielded the following results:

| Analysis | Calculated for $C_9H_{13}N_3O_4$ | Found |
|---|---|---|
| C % | 47.58 | 47.37 |
| H % | 5.73 | 5.77 |
| N % | 18.51 | 18.41 |
| O % | 28.20 | 28.26 |

Application Example 1

The following dye mixture was prepared:

| | |
|---|---|
| 2-amino-6-(β-hydroxyethyl)amino-6-(β-hydroxyethyl)amino-4-(β-aminoethyl)aminonitrobenzene | 0.125 g |
| 2-butoxyethanol | 8 g |
| COMPERLAN KD from HENKEL (diethanolamide of coprah fatty acid) | 2.2 g |
| Lauric acid | 0.8 g |
| Ethyl monoether of ethylene glycol | 2 g |
| Monoethanolamine qs pH: 10 | |
| Water qsp | 100 g |

Application of this mixture to naturally 90% white hair for 25 minutes at 35° C. produced a pale golden beige color after shampooing and rinsing.

APPLICATION EXAMPLE 2

The following dye mixture was prepared:

| | |
|---|---|
| 2-(γ-hydroxypropyl)amino-4-(γ-hydroxypropyl)-amino-6-(γ-hydroxypropyl)aminonitrobenzene | 0.067 g |
| 96° alcohol | 10 g |
| Carbopol 934 from GOODRICH CHEMICALS (reticulated polyacrylic acid) | 2 g |
| Triethanolamine qs pH: 8 | |
| Water qsp | 100 g |

Application of this mixture to bleached hair for 28 minutes at 35° C. produced an apricot color after shampooing and rinsing.

APPLICATION EXAMPLE 3

The following dye mixture was prepared:

| | |
|---|---|
| 2-methylamino-6-(β-methoxyethyl)amino-4-methoxynitrobenzene | 0.124 g |
| CELLOSIZE W.P.03 from UNION CARBIDE (hydroxyethylcellulose) | 2 g |
| Ammonium lauryl sulfate | 5 g |
| Monoethanolamine qs pH: 10 | |
| Water qsp | 100 g |

Application of this mixture to bleached hair for 30 minutes at 35° C. produced an orangey-pink color after shampooing and rinsing.

APPLICATION EXAMPLE 4

The following dye mixture was prepared:

| | |
|---|---|
| 2,6-diamino-4-hydroxynitrobenzene | 0.108 g |
| Propyleneglycol | 12 g |
| CARBOPOL 934, from GOODRICH CHEMICALS (reticulated polyacrylic acid) | 2 g |
| Monoethanolamine qs pH: 9 | |
| Water qsp | 100 g |

Application of this mixture to bleached hair for 25 minutes at 25° C. produced a straw beige color after shampooing and rinsing.

APPLICATION EXAMPLE 5

The following dye mixture was prepared:

| | |
|---|---|
| 2-methylamino-6-methylamino-4-[β-hydroxyethoxyethyl]aminonitrobenzene | 0.094 g |
| 96° alcohol | 12 g |
| CELLOSIZE W.P.03 from UNION CARBIDE (hydroxyethylcellulose) | 2 g |
| Cetyl dimethylhydroxyethyl ammonium chloride | 2 g |
| Monoethanolamine qs pH: 11 | |
| Water qsp | 100 g |

Application of this mixture to permed hair for 25 minutes at 35° C. produced an orangey-beige color after shampooing and rinsing.

APPLICATION EXAMPLE 6

The following dye mixture was prepared:

| | |
|---|---|
| 2-(β-hydroxyethyl)amino-6-(β-hydroxyethyl)amino-4-(β-aminoethyl)aminonitrobenzene | 0.1 g |
| 2-(aminoethyl)amino-4-methoxynitrobenzene hydrochloride | 0.05 g |
| 5-N,N—di(β-hydroxyethyl)amino-2-(β-aminoethyl)aminonitrobenzene | 0.043 g |
| 2-butoxyethanol | 10 g |
| ALFOL C 16/18, from CONDEA (cetylstearylic alcohol) | 8 g |
| CIRE DE LANETTE E from HENKEL (sodium cetylstearylic sulfate) | 0.5 g |
| CEMULSOL B from RHONE POULENC (ethoxylated castor oil) | 1 g |
| Oleic diethanolamide | 1.5 g |
| Triethanolamine qs pH: 8.5 | |
| Water qsp | 100 g |

Application of this mixture to 90% naturally white hair for 30 minutes at 35° C. produced a very light golden chestnut color after shampooing and rinsing.

APPLICATION EXAMPLE 7

The following dye mixture was prepared:

| | |
|---|---|
| [3-(β-hydroxyethyl)amino-5-(β-hydroxyethyl)amino-4-nitrophenyl]-β-hydroxyethylthioether | 0.1 g |
| 2-butoxyethanol | 10 g |
| LAURAMIDE from WITCO (lauric acid monoethanol amide) | 1.5 g |
| Lauric acid | 1 g |
| CELLOSIZE W.P.03 from UNION CARBIDE (hydroxyethylcellulose) | 5 g |
| Monoethanolamine qs pH: 9 | |
| Water qsp | 100 g |

Application of this mixture to bleached hair for 25 minutes at 35° C. produced a pale pink color after shampooing and rinsing.

APPLICATION EXAMPLE 8

The following dye mixture was prepared:

| | |
|---|---|
| 2-(β-hydroxyethyl)amino-6-(β-hydroxyethyl)amino-4-methoxynitrobenzene | 0.105 g |
| 2,4-di(γ-hydroxypropyl)amino-5-chloro nitrobenzene | 0.064 g |
| 5-N,N—di(β-hydroxyethyl)amino-2-(β-hydroxyethyl)aminonitrobenzene | 0.035 g |
| 96° alcohol | 10 g |
| CEMULSOL NP 4 from RHONE POULENC (4 moles O.E. nonylphenol) | 12 g |
| CEMULSOL NP 9 from RHONE POULENC (9 moles O.E. nonylphenol) | 15 g |
| Oleic alcohol, polyglycerolated, 2 moles glycerol | 1.5 g |
| Oleic alcohol, polyglycerolated, 4 moles glycerol | 1.5 g |
| Monoethanolamine qs pH: 9 | |
| Water qsp | 100 g |

Application of this mixture to bleached hair for 25 minutes at 35° C. produced a golden beige color after shampooing and rinsing.

APPLICATION EXAMPLE 9

Oxidation dye

The following dye mixture was prepared:

| | |
|---|---|
| 2-amino-6-(β-hydroxyethyl)amino-4-methoxy nitrobenzene | 1.5 g |
| Paraphenylenediamine | 0.1 g |
| Para-aminophenol | 0.07 g |
| Meta-aminophenol | 0.17 g |
| (2,4-diamino)phenoxyethanol, dihydrochloride | 0.06 g |
| 4-N—methylaminophenol, hemisulfate | 0.15 g |
| ALFOL C 16/18 from CONDEA (cetylstearylic alcohol) | 8 g |
| CIRE DE LANETTE E from HENKEL (sodium cetylstearylic sulfate) | 0.5 g |
| CEMULSOL B from RHONE POULENC (ethoxylated castor oil) | 1 g |
| Oleic diethanolamide | 1.5 g |
| MASQUOL DTPA from PROTEX (pentasodium salt of diethylene triamine pentacetic acid) | 2.5 g |
| Ammonia 22° Be | 11 g |
| Water qsp | 100 g |
| pH: 10.3 | |

At this time of use, 100 g of 20 vol hydrogen peroxide is added. Application of this mixture to bleached hair for 25 minutes at 38° C. produced a purple chestnut color after shampooing and rinsing.

We claim:

1. A substituted 2-nitro metaphenylenediamine having the formula:

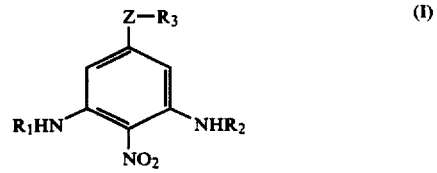

wherein Z represents the —O—, —S— or —NH— radical and $R_1$, $R_2$ and $R_3$ may be identical or different and represent a hydrogen atom or an alkyl, hydroxyalkyl, polyhydroxyalkyl, alkoxyalkyl or hydroxyalkoxyalkyl radical or an aminoalkyl radical whose amino radical may be mono- or disubstituted by an alkyl or hydroxyalkyl radical, the alkyl and alkoxy radicals containing 1 to 6 carbon atoms or cosmetically acceptable salts thereof.

2. A compound according to claim 1 wherein $R_1$, $R_2$ and $R_3$ may be identical or different and represent a hydrogen atom or a methyl, ethyl, n-propyl, n-butyl, β-hydroxyethyl, β-hydroxypropyl, γ-hydroxy propyl, β,γ-dihydroxypropyl, methoxyethyl, ethoxyethyl, β-hydroxyethoxyethyl, β-aminoethyl, β-hydroxyethylamino ethyl or β-diethylaminoethyl.

3. A compound according to claim 1 which is selected from the group comprising 2,6-diamino-4-methoxy nitrobenzene; 2,6-diamino-4-hydroxynitrobenzene; 2-(β-hydroxyethyl)amino-6-(β-hydroxyethyl)amino-4-methoxynitrobenzene; 2-[(3-methylamino-5-methylamino-4-nitro)phenoxy]ethanol; 3-[(3-methylamino-5-methylamino-4-nitro)phenoxy]propane 1,2-diol; 2-methylamino-6-(β-methoxyethyl)amino-4-methoxy nitrobenzene; 4-β-methoxyethoxy-2-(β-hydroxyethyl)amino-6-(β-hydroxyethyl)aminonitrobenzene; 2-methylamino-6-methylamino-4-(β-hydroxypropyl)amino nitrobenzene; 2-methylamino-6-methylamino-4-(β,γ-dihydroxypropyl)aminonitrobenzene; 2-methylamino-6-methylamino-4-[(β-hydroxyethoxy)ethyl]aminonitrobenzene; 2-(β-hydroxyethyl)amino-6-(β-hydroxyethyl)amino-4-(β-hydroxyethyl)aminonitrobenzene; 2-(β-hydroxyethyl)amino-4-(β-hydroxyethyl)amino-6-(β-hydroxyethyl)amino nitrobenzene; [3-(β-hydroxyethyl)amino-5-(β-hydroxyethyl)amino-4-nitrophenyl]β-hydroxyethylthioether; 2-(β,γ-dihydroxypropyl)amino-6-(β,γ-dihydroxypropyl)amino-4-methoxynitrobenzene; 2-(γ-hydroxypropyl)amino-4-(γ-hydroxypropyl)amino-6-(γ-hydroxypropyl)aminonitrobenzene and 2-amino-6-(β-hydroxyethyl)amino-4-methoxynitrobenzene.

4. A compound according to claim 2 which is selected from the group comprising 2,6-diamino-4-methoxynitrobenzene; 2,6-diamino-4-hydroxynitrobenzene; 2-(βhydroxyethyl)amino-6-(β-hydroxyethyl)amino-4-methoxynitrobenzene; 2-[(3-methylamino-5-methylamino-4-nitro)phenoxy]ethanol; 3-[(3-methylamino-5-methylamino-4-nitro)phenoxy]propane 1,2-diol; 2-methylamino-6-(β-methoxyethyl)amino-4-methoxynitrobenzene; 4-β-methoxyethoxy-2-(β-hydroxyethyl)amino-6-(β-hydroxyethyl)aminonitrobenzene; 2-methylamino-6-methylamino-4-(β-hydroxypropyl)aminonitrobenzene; 2-methylamino-6-methylamino-4-(β,γ-dihydroxypropyl)aminonitrobenzene; 2-methylamino-6-methylamino-4-[(β-hydroxyethoxy)ethyl]aminonitrobenzene; 2-(β-hydroxyethyl)amino-6-(β-hydroxyethyl)amino-4-(β-hydroxyethyl)aminonitrobenzene; 2-(β-hydroxyethyl)amino-4-(β-hydroxyethyl)amino-6-(β-hydroxyethyl)amino nitrobenzene; [3-(β-hydroxyethyl)amino-5-(β-hydroxyethyl)amino-4-nitrophenyl]β-hydroxyethylthioether; 2-(β,γ-dihydroxypropyl)amino-6-(β,γ-dihydroxypropyl)amino-4-methoxynitrobenzene; 2-(γ-hydroxypropyl)amino-4-(γ-hydroxypropyl)amino-6-(γ-hydroxypropyl)aminonitrobenzene and 2-amino-6-(β-hydroxyethyl)amino-4-methoxynitrobenzene.

5. A process for the preparation of a substituted 2-nitro metaphenylenediamine having formula (I):

(I)

wherein Z represents the —O—, —S— or —NH— radical and $R_1$, $R_2$ and $R_3$ may be identical or different and represent a hydrogen atom or an alkyl, hydroxyalkyl, polyhydroxyalkyl, alkoxyalkyl or hydroxyalkoxyalkyl radical or an aminoalkyl radical whose amino radical may be mono- or disubstituted by an alkyl or hydroxyalkyl radical, the alkyl and alkoxy radicals containing 1 to 6 carbon atoms or cosmetically acceptable salts thereof of this consisting in disubstituting a 2,4,6-trihalonitrobenzene having formula (II):

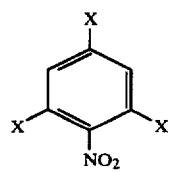

(II)

wherein X represents a halogen atom, particularly chlorine or fluorine, in order to obtain a 2,6-diamin-4-halonitrobenzene having formula (IV):

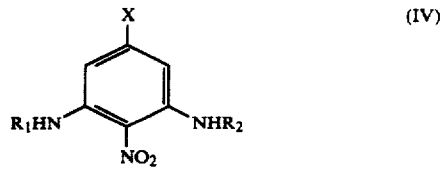

(IV)

wherein $R_1$ and $R_2$ may be identical or different and represent a hydrogen atom or an alkyl, hydroxyalkyl, polyhydroxyalkyl, alkoxyalkyl or hydroxyalkoxyalkyl radical or an aminoalkyl radical whose amino radical may be mono- or disubstituted by an alkyl or hydroxyalkyl radical, the alkyl and alkoxy radicals containing 1 to 6 carbon atoms or cosmetically acceptable salts of this compound, said substitution being effected, if necessary, in the presence of a solvent and at a temperature between −10° C. and the reflux temperature of the $R_1NH_2$ or $R_2NH_2$ amine used for the substitution or that of the solvent, then reacting the compound formula IV with a compound of formula $HZR_3$, in the presence or absence of a solvent, at a temperature of between 30° and 150° C.

6. A process for the preparation of a compound having formula (I) according to claim 5 wherein the compound having formula IV where $R_1$ and $R_2$ have different meanings is prepared by reacting, in a first stage, ammonia or an amine having formula $R_1NH_2$, $R_1$ having the meaning defined above, with the 2,4,6-trihalonitrobenzene having formula (II) having formula (II) to give a compound having formula (III):

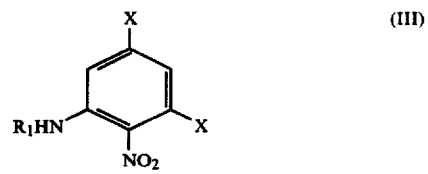

(III)

which is subsequently reacted with the $R_2NH_2$ amine or ammonia to produce the compound having formula (IV).

7. A process for the preparation of a compound having formula (I) according to claim 5, wherein the compound (IV) having identical $R_1$ and $R_2$ groups, not being a hydrogen atom, is prepared in a single stage starting from a compound having formula (II) by reaction of this compound with an amine having formula $R_1NH_2$.

8. A process for the preparation of a compound having formula (I) according to claim 5, where $R_1$ and $R_2$ represent H or alkyl, $R_3$=H and Z=O, wherein a compound of formula (I) where Z=0 and $R_3$=$CH_3$ is reacted with hydrobromic acid at a temperature of between 50° and 100° C.

9. A dye composition for keratinous fibers containing at least one substituted 2-nitro metaphenylenediamine having formula (I):

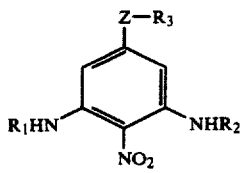

wherein Z represents the —O—, —S— or —NH— radical and R₁, R₂ and R₃ may be identical or different and represent a hydrogen atom or an alkyl, hydroxyalkyl, polyhydroxyalkyl, alkoxyalkyl or hydroxyalkoxyalkyl radical or an aminoalkyl radical whose amino radical may be mono- or disubstituted by an alkyl or hydroxyalkyl radical, the alkyl and alkoxy radicals containing 1 to 6 carbon atoms or cosmetically acceptable salts thereof.

10. A dye composition according to claim 9 containing, in a solvent medium, at least one compound selected from the group comprising 2,6-diamino-4-methoxynitrobenzene; 2,6-diamino-4-hydroxynitrobenzene; 2-(β-hydroxyethyl)amino-6-(β-hydroxyethyl)amino-4-4-nitro)phenoxy]ethanol; 3-[(3-methylamino-5-methylamino-4-nitro)phenoxy]propane 1,2-diol; 2-methylamino-6-(β-methoxyethyl)amino-4-methoxynitrobenzene; 4-(β-methoxyethoxy-2-(β-hydroxyethyl)amino-6-(β-hydroxyethyl)aminonitrobenzene; 2-methylamino-6-methylamino-4-(β-hydroxypropyl)aminonitrobenzene; 2-methylamino-6-methylamino-4-(β,γ-dihydroxypropyl)aminonitrobenzene; 2-methylamino-6-methylamino-4-[(β-hydroxyethoxy)ethyl]aminonitrobenzene; 2-(β-hydroxyethyl)amino-6-(β-hydroxyethyl)amino-4-(β-aminoethyl)aminonitrobenzene; 2-(β-hydroxyethyl)amino-4-(β-hydroxyethyl)amino-6-(β-hydroxyethyl)aminonitrobenzene; [3-(β-hydroxyethyl)amino-5-(β-hydroxyethyl)amino-4-nitrophenyl]-β-hydroxyethylthioether; 2-(β,γ-dihydroxypropyl)amino-6-(β,γ-dihydroxypropyl)amino-4-methoxynitrobenzene; 2-(γ-hydroxypropyl)amino-4-(γ-hydroxypropyl)amino-6-(γ-hydroxypropyl)aminonitrobenzene and 2-amino-6-(β-hydroxyethyl)amino-4-methoxynitrobenzene, or cosmetically acceptable salts thereof.

11. A dye composition according to claim 10, containing 0.001 to 5% by weight, preferably 0.05 to 2% by weight (with respect to the total composition weight) of at least one compound having formula (I) or one of its cosmetically acceptable salts.

12. A dye composition according to claim 11, having a pH of between 3 and 11.5, preferably between 5 and 11.5.

13. A dye composition according to claim 9 wherein the solvent is selected from water, lower alkanols, aromatic alcohols, polyols and their ethers of any mixture thereof.

14. A dye composition according to claim 9, further containing cosmetic additives selected from anionic, cationic, non ionic or amphoteric surface active agents or mixtures thereof; thickeners; dispersing agents; penetrating agents, sequestering agents, film formers, buffers, perfumes, alkalizing agents and acidifying agents.

15. A composition according to claim 9 for use in direct dyeing of human hair, additionally containing other direct dyes selected from azo dyes, anthraquinone dyes, indophenols, indoanilines and nitro derivatives of the benzene series other than those of formula (I).

16. A composition according to claim 9 for use as a setting lotion wherein it is in the form of an aqueous, alcoholic or hydroalcoholic solution containing at least one cosmetic resin.

17. A composition according to claim 9 for use in oxidation dyeing of hair, additionally containing oxidation dye precursors and, if required, couplers.

18. A direct dyeing process for keratinous fibers particularly human hair, comprising application to the fibers of a dye composition for keratinous fibers, containing at least one substituted 2-nitro metaphenylenediamine having formula (I):

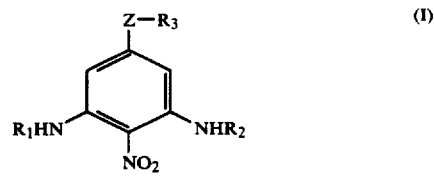

wherein Z represents the —O—, —S— or —NH— radical and R₁, R₂ and R₃ may be identical or different and represent a hydrogen atom or an alkyl, hydroxyalkyl, polyhydroxyalkyl, alkoxyalkyl or hydroxyalkoxyalkyl radical or an aminoalkyl radical whose amino radicap may be mono- or disubstituted by an alkyl or hydroxyalkyl radical, the alkyl and alkoxy radicals containing 1 to 6 carbon atoms or cosmetically acceptable salts of this compound, leaving for 5 to 50 minutes, rinsing, washing, if necessary by shampooing, rinsing again and drying.

19. A process for dyeing keratinous fibers comprising application to the washed and rinsed fibers of a dye composition for keratinous fibers containing at least one substituted 2-nitro metaphenylenediamine having formula (I):

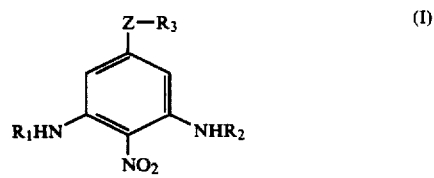

wherein Z represents the —O—, —S— or —NH— radical and R₁, R₂ and R₃ may be identical or different and represent a hydrogen atom or an alkyl, hydroxyalkyl, polyhydroxyalkyl, alkoxyalkyl or hydroxyalkoxyalkyl radical or an aminoalkyl radical whose amino radical may be mono- or disubstituted by an alkyl or hydroxyalkyl radical, the alkyl and alkoxy radicals containing 1 to 6 carbon atoms or cosmetically acceptable salts thereof for use as a setting lotion whereby it is in the form of an aqueous, alcoholic or hydroalcoholic solution containing at least one cosmetic resin, setting if required and then drying.

20. A process for dyeing keratinous fibers, involving color revelation by an oxidant, whereby a dye composition for keratinous fibers containing at least one substituted 2-nitro metaphenylenediamine having formula (I):

(I)

wherein Z represents the —O—, —S— or —NH— radical and $R_1$, $R_2$ and $R_3$ may be identical or different and represent a hydrogen atom or an alkyl, hydroxyalkyl, polyhydroxyalkyl, alkoxyalkyl or hydroxyalkoxyalkyl radical or an aminoalkyl radical whose amino radical may be mono- or disubstituted by an alkyl or hydroxyalkyl radical, the alkyl and alkoxy radicals containing 1 to 6 carbon atoms or cosmetically acceptable salts for use in oxidation dyeing of hair, additionally containing oxidation dye precursors and, if required, couplers are mixed with an oxidant and applied to the fibers, left for 10 to 50 minutes, rinsed, washed if required, rinsed and then dried.

21. The dye composition of claim 9 wherein said keratinic fibers are human hair.

22. The dye composition of claim 11 wherein said composition has a pH of between 5 and 11.5.

23. The process of claim 18 wherein said keratinic fibers are human hair.

24. The process of claim 19 wherein said keratinic fibers are human hair.

25. The process of claim 20 wherein said keratinic fibers are human hair.

* * * * *